United States Patent
Landham et al.

(12)

(10) Patent No.: US 6,841,599 B1
(45) Date of Patent: Jan. 11, 2005

(54) SOLID COMPOSITION

(75) Inventors: Rowena Roshanthi Landham, Yalding (GB); Mrinalini Sachin Oza, Yalding (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/937,596

(22) PCT Filed: Mar. 8, 2000

(86) PCT No.: PCT/GB00/00829
§ 371 (c)(1),
(2), (4) Date: Jan. 23, 2002

(87) PCT Pub. No.: WO00/59301
PCT Pub. Date: Oct. 12, 2000

(30) Foreign Application Priority Data

Apr. 1, 1999 (GB) ............................................ 9907668

(51) Int. Cl.$^7$ ........................ C08K 5/51; C08K 5/3462; C08K 3/30; C08L 37/00; A01N 25/00
(52) U.S. Cl. ...................... 524/123; 524/102; 524/423; 524/808; 524/811; 524/832; 71/27; 71/64.01
(58) Field of Search ................................ 524/102, 123, 524/423, 808, 811, 832; 71/27, 64.01

(56) References Cited

U.S. PATENT DOCUMENTS

| 4,045,204 | A | * | 8/1977 | Matsunaga et al. ............. 71/11 |
| 5,378,751 | A | * | 1/1995 | Deibig et al. ................ 524/414 |
| 5,766,615 | A | * | 6/1998 | Narayanan ................... 424/405 |
| 6,528,569 | B1 | * | 3/2003 | Oza et al. .................... 524/442 |

FOREIGN PATENT DOCUMENTS

| GB | 2 095 558 A | * | 10/1982 |
| WO | 9323999 | | 12/1993 |
| WO | WO 94/23573 | * | 10/1994 |
| WO | 9731528 | | 9/1997 |
| WO | 9959407 | | 11/1999 |

* cited by examiner

Primary Examiner—Tae H. Yoon
(74) Attorney, Agent, or Firm—Thomas Hamilton

(57) ABSTRACT

A solid, water-soluble or water-dispersible composition comprising a non film-forming material (such as a water-soluble agrochemical) supported by a film-forming polymer is prepared by (i) preparing a film-forming aqueous medium containing (a) a film-forming polymer which is a partially or fully charged homopolymer or a partially charged block copolymer or a homopolymer or block copolymer capable of ring-opening to form a partially charged homopolymer or block copolymer and (b) a water soluble material which is non film-forming (such as a glyphosate salt) and thereafter (ii) drying the film-forming aqueous medium to form the solid composition. The preferred film-forming polymer is alkyl vinylether maleic anhydride block co-polymer or a hydrolysed form thereof.

8 Claims, No Drawings

US 6,841,599 B1

SOLID COMPOSITION

This invention relates to a solid composition and to a process for preparing a solid composition and in particular to a process for preparing a solid, water-soluble or water-dispersible composition containing a water-soluble material which is not film-forming and a film-forming water soluble material.

Film-forming polymers are used in a number of industries to provide a solid polymer medium within which a second non film-forming component may be supported. Typical of such applications is the casting of an aqueous solution of the film-forming polymer to form polymer sheets (tapes) or flakes.

Thus for example in WO 93/23999 there is disclosed a packaging for storing and releasing incompatible crop protection materials in which a chemical is "encapsulated" or supported in a water-soluble polymer film.

Such processes typically involve as a first step dissolving a film-forming polymer in water to form an aqueous film-forming medium in which a material to be supported is dissolved or suspended. The film-forming medium is then for example cast onto a suitable substrate and dried to form a solid tape containing the material to be supported. Under certain conditions the tape may loose coherence during drying to form flakes. Alternatively, the film-forming medium can be dried to produce granules, agglomerates or powders.

We have found however that problems may arise when the non film-forming material to be supported is itself water-soluble, particularly if it is a strong electrolyte. Specifically, we have found that the presence of a water-soluble electrolyte in an aqueous solution of a conventional film-forming polymer tends to interact adversely with the polymer at the relatively high polymer concentration required to provide adequate film-forming properties. As a result the film-forming polymer may be thrown out of solution as a rubbery deposit, and even quite small concentrations of water-soluble electrolyte may have a deleterious effect on the film-forming properties and homogeneity of the medium. The problem is exacerbated if the water-soluble electrolyte is hygroscopic such that even if a solid composition can be formed, it tends to pick up water causing the film-forming polymer component to become sticky.

In our co-pending United Kingdom Patent Application No 9810861.6 there is described a process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer (b) a water soluble material which is non film-forming and (c) a water-miscible solvent in which the film-forming polymer is soluble and thereafter (ii) drying the film-forming aqueous medium to form the solid composition. We have now found a specific class of polymers which are compatible even with a water soluble electrolyte and which do not require the use of a water-miscible solvent in which the film-forming polymer is soluble. Those skilled in the art will appreciate the significant process advantages in being able to avoid the use of a water miscible co-solvent such as an alcohol.

Thus according to the present invention there is provided a process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer which is a partially or fully charged homopolymer or a partially charged block copolymer or a homopolymer or block copolymer capable of ring-opening to form a partially charged homopolymer or block copolymer and (b) a water soluble material which is non film-forming and thereafter (ii) drying the film-forming aqueous medium to form the solid composition.

Suitably the film-forming aqueous medium is prepared using water as the sole medium (solvent or dispersant) for both the film-forming polymer (a) and the water-soluble material (b), and in particular in the substantial absence of a water miscible solvent in which the film-forming polymer is soluble.

Whilst the process of the present invention may be applied to any water-soluble material which is not film-forming and which is suitable for being supported in a solid composition of a film-forming polymer, it is of particular relevance when the water-soluble supported material is a strong electrolyte and even more particularly when the water-soluble supported material, in its dry form, is hygroscopic. Typical strong electrolytes are salts, for example salts of an organic acid or base. The scope of the present invention is not restricted to a water-soluble supported material having a specific utility, although it is illustrated herein with reference to a water-soluble supported material having utility in the agrochemical field, either as an active agrochemical or as an agrochemical adjuvant. Typical examples of water-soluble active agrochemicals which are strong electrolytes are salts of glyphosate, including without limitation the trimethylsulphonium salt, the isopropylamine salt, the sodium salt, the potassium salt and the ammonium salt and bipyridylium salts such as paraquat dichloride or diquat dibromide, glufosinate and fomesafen.

Typical examples of agrochemical adjuvants which are strong electrolytes are organic or inorganic salts such as ammonium sulphate. The process of the present invention provides a convenient method of obtaining a solid formulation of an agrochemical or an agrochemical adjuvant or an agrochemical formulation containing both active agrochemical and adjuvant having advantages in respect of handling, storage, transportation and reduced container contamination. Typical solid formulations of the present invention such as tapes or flakes provide a convenient delivery vehicle for the agrochemical or agrochemical formulation and may be arranged for example such that a single unit dose of agrochemical is contained in a unit dose package, for example in a conventional unit dose package or in water-soluble sachet packaging. If the process of the present invention is used to form a cast tape, the tape may be cut to provide a length corresponding to a desired dose. Furthermore we have found that the process of the present invention may be used to provide solid compositions containing a high loading of agrochemical or agrochemical adjuvant and in many instances a higher loading than would be possible in the absence of water-miscible solvent or with conventional water-soluble polymers. In certain circumstances the process of the present invention may be used to provide a solid composition containing an agrochemical formulation whose individual components are incompatible or show long-term physical instability if used in the form of an aqueous liquid concentrate. Thus for example it may be possible to use a higher content of an adjuvant such as ammonium sulphate than would be compatible as an aqueous liquid concentrate formulation of an agrochemical.

The term "film-forming" polymer indicates that the polymer is capable of providing film-forming properties in the presence of water. The film-forming polymer will generally be at least partially water-soluble but could also provide a film-forming aqueous medium in which the film-forming polymer is present in the form of a dispersion, and in particular a colloidal dispersion or in the form of a sol or latex or in the form of a solution containing some dispersed material. Alternatively, as described below, an insoluble form of homopolymer or blockcopolymer may be converted to a soluble or partially soluble form under the process conditions.

By the term "a partially or fully charged homopolymer or a partially charged block copolymer" is meant a homopolymer or block copolymer having anionic functional units such as carboxylic acid or sulphonic acid functional units or a mixture of such anionic functional units associated with a suitable cation or cationic functional units such as an alkali or alkaline earth cation, for example a sodium cation. If desired the charged, anionic, functional unit may be generated in situ for example by ring opening of an uncharged block co-polymer or homopolymer.

An especially suitable block copolymer capable of ring opening to form a partially charged block copolymer is an alkyl vinylether maleic anhydride block copolymer which is capable of ring opening in water, particularly under basic conditions or in the presence of suitable species to form a dicarboxylic acid or its derivatives such as salts or partial esters. Dicarboxylic acid derivatives of an alkyl vinyether maleic anhydride blockcopolymer and their salts and partial esters are preferred examples of a partially charged block copolymer.

The alkyl vinylether maleic anhydride block copolymer and its partially charged derivatives are preferably lower ($C_1$ to $C_4$) alkyl vinylether maleic anhydride block copolymers for example methyl vinylether maleic anhydride block copolymers. Such copolymers are based on strictly alternating copolymers of alkyl vinyl ether and maleic anhydride which may be combined to produce products of various molecular weights. A methyl vinyether maleic anhydride block copolymer has the general formula (I) in which the value of n indicates the molecular weight (degree of polymerisation).

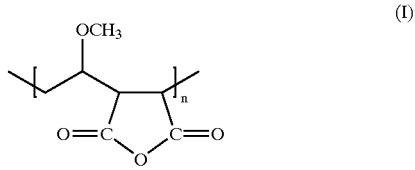

(I)

In general the block copolymer will consist of a mixture having different degrees of polymerisation and n normally represents an average value corresponding to an average molecular weight.

Methyl vinylether maleic anhydride block copolymer is essentially insoluble in water but hydrolyses slowly to give the acid form. This hydrolysis is more rapid under basic conditions or in the presence of suitable species, as illustrated in Reaction Scheme I.

Reaction Scheme 1

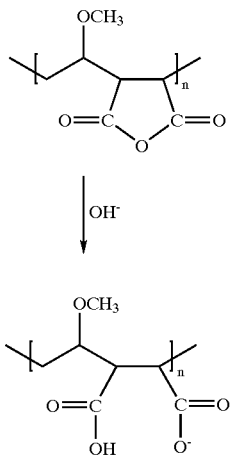

As examples of fully or partially charged block co-polymers suitable for use in the process of the present invention there may be mentioned salts of co-polymers, such as the sodium salt of poly (acrylic acid/maleic acid) copolymer and salts such as the sodium salt of sulphonated poly (styrene/maleic anhydride) copolymer. As examples of partially or fully charged homopolymers suitable for use in the process of the present invention there may be mentioned salts, for example alkali metal salts of acidic homopolymers or of sulphonated homopolymers, for example the sodium salt of sulphonated polystyrene, the sodium salt of sulphonated polyvinyl alcohol, the sodium salt of polyacrylic acid and the sodium salt of polymethacrylic acid.

The process of the present invention is especially well suited to the production of a solid formulation of a glyphosate system and in particular a glyphosate system containing an ammonium salt such as ammonium sulphate as adjuvant. We have found that, surprisingly, there is no need to include an inert filler in the composition if ammonium sulphate is present in the preferred proportions. Whilst it is possible to adjust the pH of the system by the addition of a suitable base, it is especially convenient to employ a glyphosate system in which the pH is already in the desired range. An especially suitable glyphosate system is an ammonium glyphosate system and preferably an ammonium glyphosate system containing an ammonium salt such as ammonium sulphate. Whilst the ammonium ion present in such a composition should not be thought of as being associated specifically with either the glyphosate anion or for example the sulphate anion, it is convenient to express the concentration of ammonium ion relative to glyphosate ion as being in addition to that which may also be present in the "ammonium salt". Thus the molar ratio of ammonium ion (in excess of that in the "ammonium salt") to glyphosate is preferably from 1:1 to 2:1, for example from 1.7:1 to 1.9:1. These ratios correspond to a pH of from about 3.5 to 6.6 and from about 5.7 to 6.2 respectively.

We have found that if solid, powdered methyl vinylether maleic anhydride block copolymer is added to an aqueous solution of ammonium ions and glyphosate ions at a ratio as indicated above, and the mixture is allowed to stand, for example for about 30 minutes, a clear solution is formed. It is believed that the methyl vinylether maleic anhydride block copolymer has undergone ring opening to the soluble dicarboxylic acid form. We have found that the solution is initially of relatively low viscosity but that the viscosity increases on standing. Whatever the reason for the observed viscosity behaviour, this behaviour may be used to advantage in process terms and there may therefore be a benefit in the use of the unhydrolysed methyl vinylether maleic anhydride block copolymer as starting material as opposed to using the hydrolysed material from the start. Thus whilst it is believed that the process of the present invention involves the solubilisation of an alkyl vinylether maleic anhydride block copolymer via ring opening under alkaline conditions or in the presence of an suitable species such as those present in solution of ammonium glyphosate, the scope of the present invention is not limited by any such theory. Regardless of the precise mechanism involved, it is observed that an alkyl vinylether maleic anhydride block copolymer is soluble for example in ammonium glyphosate solutions used in the process of the present invention and forms a stable film-forming medium. A preferred process according to the invention is thus a process wherein the water-soluble material is a salt of glyphosate, the film-forming medium is an alkyl vinylether maleic anhydride co-polymer and there is incorporated in the film-forming medium an ammonium salt, preferably in the substantial absence of an inert filler.

Thus according to a further aspect of the present invention there is provided a process for producing a solid, water-soluble or water-dispersible composition comprising a glyphosate herbicide supported by a film-forming polymer which process comprises (i) preparing a film-forming aqueous medium containing (a) a film-forming polymer which is an alkyl vinylether maleic anhydride block copolymer, (b) an ammonium salt of glyphosate and optionally (c) ammonium sulphate and (ii) drying the film-forming aqueous medium to form the solid composition.

If desired the film-forming aqueous medium formed in stage (i) may be allowed to stand until a clear solution is formed or until hydrolysation is substantially complete or until a desired viscosity increase takes place. Preferably the ammonium sulphate is present in the substantial absence of an inert filler.

It may be desirable to include a filler such as an inert inorganic filler in the solid composition. As noted above, it is an unexpected advantage of the process of the present invention however that an ammonium salt such as ammonium sulphate may be used both as adjuvant for an active material such as glyphosate and also as filler. If desired however an inert filler may be used in addition to or instead of ammonium sulphate. The inert filler is preferably a water-dispersible solid inorganic or organic filler such as calcium silicate, magnesium silicate (talc), sodium aluminium silicate, silica, mica, cellulosic fibre such as wood fibre, starch and diatomaceous earth. It is especially preferred that a highly adsorptive filler is used, for example a filler having a high surface area for example a surface area greater than 5 $m^2/g$ and preferably greater than 80 $m^2/g$. Ultra-fine fillers such as fumed silica are not generally satisfactory however. As a specific example of a suitable filler there may be mentioned CALFLO E (CALFLO is a trade mark World Minerals), a calcium silicate filler having a surface area of about 100 $m^2/g$.

The film-forming aqueous medium is preferably formed by first dissolving the film-forming polymer in the relevant aqueous medium. Thus by way of example, a film-forming aqueous medium containing ammonium ions glyphosate ions and sulphate ions may conveniently be prepared by the following method:

1. Methyl vinylether maleic anhydride is added as a solid to an aqueous solution containing ammonium ions and glyphosate ions (for example containing about 40% by weight based on glyphosate acid). On mixing and standing a colourless solution of relatively low viscosity is formed.
2. To this solution is optionally added a surfactant if used either to provide biological enhancement of the glyphosate or to affect the surface tension properties of the film-forming aqueous medium relative to a substrate on which it is cast.
3. The desired proportion of finely ground solid ammonium sulphate is added next. In general the volume of water present will not be sufficient to dissolve all the ammonium sulphate, but since the ammonium sulphate is acting in part as inorganic filler this does not represent a problem.

The above order of addition is not essential but is preferred since it ensures that the methyl vinylether maleic anhydride copolymer is added to an appropriate medium comprising a component to ensure hydrolysis (i.e. the ammonium glyphosate). The other components may be added whilst the viscosity is relatively low, whilst if the viscosity increases on standing it may have beneficial effects in terms of even dispersion of any undissolved ammonium sulphate and in terms of film-forming properties.

The resultant film-forming aqueous medium is then dried to form a solid composition. The physical form of the resultant solid composition will depend on the exact manner of drying of the film-forming aqueous medium and a wide variety of processes may be used to provide a wide range of solid products. For example simple drying of the film-forming aqueous medium will generally form a powder or agglomerate. Greater control of the formation of a powder or granule product may be obtained by spray drying or freeze drying of the film-forming aqueous medium. The film-forming medium may be partially or wholly formed into fibres, for example by being extruded into a fast-moving stream of air, and the resultant solid composition may take the form of fibres or of a uniform particulate composition resulting from the breaking up of such fibres on further drying. The film forming aqueous medium can also be applied on an anti-adherent, rotating drum surface by means of a roller and subsequently dried by hot air to yield dry flakes. Alternatively the film-forming material may be cast in the form of a film onto a substrate, for example a conveyor belt, from which it is preferably removed after drying.

The casting of the film-forming aqueous medium onto a substrate may take place using conventional techniques such as tape casting. In tape casting, a film is formed on a substrate and the thickness is adjusted to that required using a device such as a "doctor blade" which defines a predetermined space between the surface of the substrate and the knife of the doctor blade. The substrate is conveniently a flat, planar surface but may also if desired possess indentations to provide appropriate corresponding patterning on the surface on the film. Similarly, the "doctor blade" may have a contoured knife to provide corresponding patterning on the top surface of the film. In the extreme, the substrate may comprise one or more wells into which the film-forming aqueous medium is cast so that discrete pellets or tablets are formed on drying.

In commercial practice, it is normal to supply the film-forming medium from a reservoir and to form the film continuously, for example by the use of a moving belt as substrate or by movement of a reservoir and associated doctor blade relative to a stationary substrate. In commercial practice it is usually convenient to use a metal substrate although a plastics substrate may be used if desired.

The cast medium may be dried under atmospheric conditions but it is more conveniently dried at elevated temperature. In general it is sufficient to dry the cast medium at a temperature of from ambient to 100° C., for example from 40 to 60° C. It is to be understood that the drying process will not necessarily remove all traces of water and of the solvent for the film-forming polymer, and indeed a small proportion of residual water or solvent in the dry, cast product may have a beneficial plasticising effect. Typically levels of water in the range of 0.1 to 20% by weight are to be expected in the dry, cast product. Heating may be achieved for example by passing the cast medium into an oven or heated space or by applying heat to the substrate. Once the cast medium is dried, it may be removed from the substrate for subsequent use.

The cast medium may be removed from the substrate as a coherent sheet (a cast tape) and the coherent sheet may if desired subsequently be subdivided, for example by cutting, punching, or flexing to form flakes or shaped forms. Alternatively the proportions of the components of the film-forming medium, for example the content of the solid filler, may be selected such that the cast medium looses coherency during drying and cracks with the formation of flat flakes of product.

The thickness of the cast product, for example the cast tape or flakes, may be varied within wide limits according to the desired application. Typically the thickness of a cast tape or flakes varies between about 0.04 mm to 5 mm depending on the flexibility and other characteristics desired. If flakes are not formed directly, the dry tapes can be cut or fashioned to include a wide variety of shapes and designs, including for example discs, flakes, strips, tubes and spirals. The tape can be cut to provide a pre-determined metered dose of active ingredient which simplifies the formation of a dilute agrochemical spray for example. The tapes may also be embossed, corrugated or patterned to increase the surface area and may also carry printed information such as product and safety information.

For certain applications it may be desirable to protect the surface of the cast, dry product. The surface of the cast product may readily be protected by lamination or co-casting with a layer of water-soluble polymer which contains no active product and which may be the same as or different from the film-forming polymer. Alternatively, the cast, dry product may be housed in a water-soluble bag which may be manufactured from the same or different water-soluble polymer.

The proportions of the components of the solid composition formed by the process of the present invention may be varied widely depending on factors such as (a) the desired content of the active material in the solid composition (b) the process used to obtain the solid product and the desired properties of the aqueous film-forming medium and (c) the desired properties (such as dispersibility) of the resultant solid composition.

Thus for example if the film-forming aqueous medium is to be used to form a cast tape or cast flakes, a relatively higher film-forming level of polymer is likely to be required in the film-forming aqueous medium as compared with the film-forming aqueous medium used for spray-drying. Similarly a more coherent product is likely required if the final product is to be a cast tape rather than flakes. Such a coherent product is likely for example to require a relatively higher proportion of film-forming polymer as compared with the solid filler content. In general, sufficient of the film-forming polymer should be used to form a film-forming aqueous medium, by which is meant an aqueous medium having a suitable rheology and in particular a suitable viscosity for the drying process selected, for example for casting on a substrate. If there is insufficient polymer in solution, the aqueous medium will tend to run off the substrate and form too thin a film. If on the other hand too much polymer is present in the aqueous medium, it will not flow smoothly and the resultant film will not be self-levelling and uniform. The optimum concentration of polymer to provide an effective film-forming aqueous medium will vary depending on the exact nature and grade of polymer used but may be determined by simple and routine experimentation. Typical concentrations are illustrated in the Examples. Thus for example the concentration of the film-forming polymer in the film-forming aqueous medium typically from 0.5 to 95% by weight, for example from 1 to 50% by weight. It will be appreciated however that one skilled in the art may readily determine the optimum concentration of film-forming polymer for any given process method.

As noted above, it is a particular advantage of the process of the present invention that a high loading of the water-soluble supported material may if desired be obtained in the solid composition. For example in favourable circumstances greater than about from 40% or 50% and even up to as high as 75% or more by weight of a water-soluble supported material such as an agrochemical active ingredient may be incorporated in the solid composition of the invention. This itself carries with it a further advantage in that potential problems of poor dispersion of the solid composition in water may be greatly reduced when a major proportion of the solid composition is the water-soluble agrochemical. It may thus for example be possible to use a film-forming polymer or other components which would otherwise give rise to dispersion problems if used at higher concentrations or if used in conjunction with water-soluble insoluble components. It is of course possible to use lower proportions of water-soluble supported material, for example 20% or less by weight, if desired but some of the advantages of the present invention may not be so apparent in such products. Furthermore, if an inorganic adjuvant such is ammonium sulphate is used in conjunction with a water-soluble is agrochemical electrolyte, it is possible to combine high loadings of the agrochemical electrolyte such as a glyphosate salt with high loadings of ammonium sulphate, thus overcoming a severe stability problem which is commonly encountered when glyphosate is used with ammonium sulphate in aqueous concentrates.

According to a further aspect of the present invention there is provided a solid, water-dispersible or water soluble composition comprising a water-soluble agrochemical electrolyte, a film-forming polymer which is a homopolymer or a partially charged block copolymer or a block copolymer capable of ring opening to form a partially charged block copolymer and a filler which is an ammonium salt.

According to a still further aspect of the present invention there is provided a solid water-dispersible or water soluble composition comprising a glyphosate salt, an alkyl vinylether maleic acid copolymer or a hydrolysed derivative thereof and ammonium sulphate.

According to a still further aspect of the present invention there is provided a solid water-dispersible or water soluble composition comprising ammonium glyphosate, methyl vinylether maleic acid copolymer or a hydrolysed derivative thereof and ammonium sulphate.

One skilled in the art will readily be able to determine appropriate proportions for each desired application but further detail is now given for the purposes of illustration only.

The proportion of polymer necessary to provide the required film-forming properties of the aqueous medium depends, at least in part, on the molecular weight of the polymer. We have found for example that methyl vinylether maleic acid copolymer having a number average molecular weight of from 20,000 to 990,000 for example a number average molecular weight of from 100,000 to 300,000 for example from about 200,000 to about 250,000 is particularly suitable for the process of the present invention. If hydrolysed methyl vinylether maleic acid copolymer is used as starting material, the molecular weight may be higher than that of the corresponding unhydrolysed precursor and number average molecular weights up to 3,000,000 may be used without detriment.

In general, we have found for example that for cast flake products, it is desirable to use a minimum of about 2% by weight of methyl vinylether maleic acid anhydride or hydrolysed product thereof having a molecular weight of between about 100,000 and 300,000 to achieve coherent flakes. There is no real upper limit to the proportion methyl vinylether maleic acid anhydride which may be used but generally there is little advantage in a product having high levels of film-forming polymer and low levels of supported material. The proportion of film-forming polymer in the final product is thus typically from 2% to 20% by weight.

We have found that surprisingly it is possible to use a non-absorptive, water soluble inorganic filler such as ammonium sulphate as filler in the solid formulations. The upper limit of the proportion of inorganic solid such as ammonium sulphate is generally determined by the biological activating effect which it is desired to achieve and in particular the desired glyphosate to ammonium sulphate ratio in the spray solution. There is little advantage in a product having excessively high levels of inorganic filler over and above that desired to achieve the desired biological effect, and the proportion of inorganic filler in the final product is thus typically from 1% to 90% by weight, for example from 2% to 50% by weight.

If desired, other components may be added to the film-forming aqueous medium. Thus for example it may be desirable, particularly if the cast product is to be a cast tape (a film), to include a plasticiser to improve the flexibility of the cast product. Suitable plasticisers include glycerols, $C_2$ to $C_6$ glycols and polyglycols such as polyethylene glycol, dialkyl phthalates such as dioctyl phthalate, sorbitol and triethanolamine or mixtures thereof. In addition to improving the flexibility of the product a plasticiser may also have an advantageous effect on the rate of dispersion of the dry, cast product in water. The proportion of plasticiser is preferably within the range 0 to 80% by weight, for example from 5 to 30% by weight relative to the film-forming polymer.

Surfactants may be added to the film-forming aqueous medium both to enhance the rate of dispersion of the dry product in water and also to affect the surface tension properties of the film-forming aqueous medium relative to a substrate on which it is cast. Thus for example a wetter may be added to ensure wetting of the substrate, for example if a plastics substrate is used. If it is desired to produce cast tapes rather than flakes, surfactants may also be added which modify the surface tension of the wet cast film and ensure that on drying the film reduces in thickness with minimum shrinkage in the plane of the substrate on which it is cast. A wide variety of surfactants may be used for these purposes and suitable examples will occur to one skilled in the art. Solid surfactants are generally preferred to liquid since they may be present in relatively high loading in the cast product.

If the product is a solid formulation of an agrochemical electrolyte it will generally be desirable to add a surfactant to provide adjuvant properties in the final application, for example as a wetter or biological enhancing agent. Very many adjuvants, for example adjuvants enhancing biological activity, are know to those skilled in the art and in general conventional adjuvants may be incorporated in the process of the present invention without detriment. Typical adjuvants are illustrated in the Examples but the selection of such adjuvants does not form part of the present invention and many such may be used. It will be appreciated however that, as with any agrochemical formulation, not all conventional adjuvants will be compatible, particularly if used at high concentration.

An antifoam agent may be added to prevent excessive aeration during mixing of the film-forming aqueous medium. A viscosity aid may be added if desired to modify the viscosity of the film-forming aqueous medium, for example to minimise any settling of the solid filler within the thickness of the wet film during drying. Suitable viscosity-modifying aids include alginates, starch, gelatin, natural gums, hydroxyethyl cellulose, methyl cellulose, silica and clays.

According to a further aspect of the present invention there is provided a solid water-soluble or water-dispersible composition whenever prepared by a method according to the present invention.

The film-forming polymer which is a partially charged homopolymer or a partially charged block copolymer or a homopolymer or block copolymer capable of ring-opening to form a partially charged-homopolymer or block copolymer and in particular the copolymer of methyl vinly ether/maleic anhydride or its hydrolysed or otherwise water-soluble derivative may provide additional advantageous effects in the aqueous spray solution. Such advantageous effects may include for example enhanced rainfastness and reduced spray drift. Such beneficial effects will be achieved of course whether the polymer is introduced as a result of the dissolution of a solid composition of the present invention or otherwise. Thus for example the polymer may be added directly to the aqueous spray solution either as a solid or more preferably as an aqueous solution or may included in an aqueous concentrate intended for dilution prior to use. The introduction of spray-drift reducing or rainfastness enhancing polymers has hitherto encountered compatibility problems, especially when used in conjunction with electrolytes such as glyphosate and paraquat salts. Such compatibility problems which are acute in the film-forming compositions of the present invention are found even in more dilute solutions.

Thus according to a further aspect of the present invention there is provided an aqueous spray solution or an aqueous concentrate of an agrochemical electrolyte such as a glyphosate or paraquat salt comprising a polymer which is a partially charged homopolymer or a partially charged block copolymer or a homopolymer or block copolymer capable of ring-opening to form a partially charged-homopolymer or block copolymer and in particular a copolymer of methyl vinly ether/maleic anhydride or its hydrolysed or otherwise water-soluble derivative.

The invention is illustrated by the following Examples in which all parts and percentages are by weight unless otherwise stated.

EXAMPLE 1

AGRIMIER VEMA AN-216 (0.5 g, a copolymer of methyl vinly ether/maleic anhydride having a number average molecular weight of about 216,000 to 230,000; AGRIMER is a trade mark of ISP (Great Britain) Co. Ltd.) was added to ammonium glyphosate (9.0 g of an aqueous solution containing 40% by weight glyphosate acid equivalent and a molar ratio of ammonia to glyphosate acid of 1.75:1), stirred manually and allowed to stand for approximately 20 minutes until the polymer had dissolved. To this solution, MERGITAL LM17 (1.2 g, $C_{10/14}$ alcohol ethoxylate with 17 moles EO, MERGITAL is a trademark of Henkel) and ammonium sulphate (4.3 g, pre-ground to a fine powder using a mortar and pestle) were added. The resultant dispersion was mixed thoroughly over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 39.8% glyphosate salt (36.1% glyphosate acid equivalent), 5.0% copolymer, 12.0% Mergital LM17 and 43.2% ammonium sulphate. The foregoing calculations are based on the assumption of an ammonia:glyphosate ratio of 1:1 in the solid (over and above the ammonium sulphate content). If this assumption is incorrect, the figures are still indicative of the relative proportions in the solid.

When a sample of flakes (5.63 g) was exposed to ambient conditions (21° C. temperature, 66% relative humidity) in an open petri dish for 72 hours, it did not deliquesce. The weight gain due to moisture pick-up under these conditions was 1.6% in a sample which had been pre-dried for 24 hours in an oven maintained at 50° C.

The dispersion time as measured by the standard test method given below for a 0.50 mm thick (0.22 g) sample was approximately 60 seconds.

The dispersion time of the solid was measured in a standard test by dropping a sample of between 4 and 10 flakes (of dimension 2 mm×2 mm) into a boiling tube (of approximate dimensions 8 inches×1 inch, with a water tight stopper) filled with tap water at 20° C.±1° C. to leave an ullage space of 0.5 to 0.75 inches in the tube. The tube was inverted slowly such that the flakes are not allowed to sit on the bottom of the tube but are allowed to settle through the medium under the influence of gravity. The time taken for the flakes to completely disperse was noted.

EXAMPLE 2

AGRIMER VEMA AN-216 (0.5 g) was added to ammonium glyphosate (9.0 g of an aqueous solution containing 40% acid equivalent and an ammonia to glyphosate acid molar ratio of 1.75:1.00), stirred manually and allowed to stand for approximately 20 minutes until the polymer had dissolved. To this solution, ETHOMEEN T25 (1.2 g, Tallowamine ethoxylate with 15 moles EO from Akzo Nobel Chemicals) and ammonium sulphate (4.3 g, pre-ground to a fine powder using a mortar and pestle) were added. The resultant dispersion was mixed thoroughly over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 39.8% glyphosate salt (36.1% glyphosate acid equivalent), 5.0% copolymer, 12.0% ETHOMEEN T25 and 43.2% ammonium sulphate.

When a sample of flakes (4.76 g) was exposed to ambient conditions (21° C. temperature, 66% relative humidity) in an open petri dish for 72 hours, it did not deliquesce. The weight gain due to moisture pick-up under these conditions was 1.5% in a sample which had been pre-dried for 24 hours in an oven maintained at 50° C.

The dispersion time, as measured by the standard test method, for a 0.61 mm thick (0.29 g) sample was approximately 93 seconds.

EXAMPLE 3

AGRIMER VEMA AN-216 (1.5 g) was added to ammonium glyphosate (22.5 g of an aqueous solution containing 40% acid equivalent and a molar ratio of ammonia to glyphosate acid of 1.75:1.00), stirred manually and allowed to stand for approximately 20 minutes until the polymer had dissolved. To this solution, Mergital LM17 (3.0 g) and ammonium sulphate (10.5 g, pre-ground to a fine powder using a mortar and pestle) were added. The resultant dispersion was mixed thoroughly over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 39.8% glyphosate salt (36.1% glyphosate acid equivalent), 6.0% copolymer, 12.0% Mergital LM17 and 42.2% ammonium sulphate.

The solid was dissolved in water and the resultant solution showed excellent bioefficacy when tested against standard plant species.

EXAMPLE 4

AGRIMER VEMA AN-216 (0.6 g), AEROSOL OT-B {0.2 g, sodium dioctylsulphosuccinate (85%) and sodium benzoate (15%); AEROSOL is a trademark of American Cyanamid Company}, CALFLO E (3.0 g, a high surface area calcium silicate filler—CALFLO is a trademark of World Minerals) were added to ammonium glyphosate (22.0 g of an aqueous solution containing 40% acid equivalent and an ammonia to glyphosate acid molar ratio of 1.75:1.00), stirred manually and allowed to stand for approximately 30 minutes until the polymer had dissolved. The resultant dispersion was mixed thoroughly over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 71.8% glyphosate salt (65.3% glyphosate acid equivalent), 4.5% copolymer, 1.5% Aerosol OT-B and 22.2% CALFLO E.

When a sample of flakes (4.4 g) was exposed to ambient conditions (27–29° C. temperature, 35–57% relative humidity) in an open petri dish for 24 hours, it did not deliquesce. The weight gain due to moisture pick-up under these conditions was 1.4% in a sample which had been pre-dried for 24 hours in an oven maintained at 50° C.

The dispersion time, as measured by the standard test method, for a 0.40 mm thick (0.34 g) sample was approximately 180 seconds.

EXAMPLE 5

Ammonium sulphate (2.8 g, pre-ground to a fine powder using a mortar and pestle) was added to ammonium glyphosate (22.0 g of an aqueous solution containing 40% acid equivalent and an ammonia to glyphosate acid ratio of 1.75:1.00). AGRIMER VEMA AN-216 (1.0 g) and Aerosol OT-B (0.25 g) were then added and the dispersion stirred manually and allowed to stand for approximately 20 minutes until the polymer had dissolved. The resultant dispersion was mixed thoroughly over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 70.5% glyphosate salt (64.1% glyphosate acid equivalent), 7.3% copolymer, 20.4% ammonium sulphate and 1.8% Aerosol OT-B.

When a sample of flakes (5.74 g) was exposed to ambient conditions (21° C. temperature, 66% relative humidity) in an open petri dish for 72 hours, it did not deliquesce. The weight gain due to moisture pick-up under these conditions was 4.5% in a sample which had been pre-dried for 24 hours in an oven maintained at 50° C.

The dispersion time, as measured by the standard test method, for a 0.49 mm thick (0.17 g) sample was approximately 48 seconds.

EXAMPLE 6

AGRIMER VEMA AN-216 (3.1 g) was added to ammonium glyphosate (51.2 g of an aqueous solution containing 40% acid equivalent and an ammonia to glyphosate acid molar ratio of 1.75:1.00), stirred manually and allowed to stand for approximately 20 minutes until the polymer had dissolved. To this solution, Mergital LM17 (0.4 g) and ammonium sulphate (4.2 g, pre-ground to a fine powder using a mortar and pestle) were added. The resultant dispersion was mixed thoroughly over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 74.5% glyphosate salt (67.7% glyphosate acid equivalent), 10.3% copolymer, 1.3% Mergital LM17 and 13.9% ammonium sulphate.

The solid was dissolved in water and the resultant solution showed satisfactory bioefficacy when tested against standard plant species.

EXAMPLE 7

Glyphosate trimesium (11.9 g of an aqueous solution containing 60.5% salt–41.7% glyphosate acid equivalent) was added to AGRIMER VEMA AN-216 (1.2 g), stirred manually and allowed to stand for approximately 1 hour. To this solution, MERGITAL LM17 (2.4 g) and ammonium sulphate (7.6 g, pre-ground to a fine powder using a mortar and pestle) were added. The resultant dispersion was mixed thoroughly over a period of 5 minutes until a homogenous, viscous slurry was produced.

The viscous film-forming medium was cast onto a polymer film (polythene) substrate using a "doctor blade" set at a blade height of 0.75 mm. The cast tape was dried in an oven maintained at 70° C. and the solid stripped from the substrate as a strong, flexible tape.

The resultant solid contained 39.1% glyphosate salt (27.0% glyphosate acid equivalent), 6.5% copolymer, 13.1% Mergital LM17 and 41.3% ammonium sulphate.

EXAMPLE 8

Potassium glyphosate (26.6 g of an aqueous solution containing 48.1% by weight of glyphosate acid equivalent and a molar ratio of potassium to glyphosate acid of 1.13:1), was added to AGRIMER VEMA AN-216 (1.5 g), stirred manually and allowed to stand for approximately 30 minutes. To this mixture, Aerosol OT-B (0.4 g) and ammonium sulphate (2.0 g, pre-ground to a fine powder using a mortar and pestle) were added. The resultant dispersion was mixed thoroughly over a period of 5 minutes until a homogenous, viscous slurry was produced.

The viscous film-forming medium was cast onto a polymer film (polythene) substrate using a "doctor blade" set at a blade height of 0.75 mm. The cast tape was dried in an oven maintained at 70° C. and the solid stripped from the substrate as a brittle tape.

The resultant solid contained 80.4% glyphosate salt (64.3% glyphosate acid equivalent), 7.5% copolymer, 2.0% Aerosol OT-B and 10.1% ammonium sulphate.

EXAMPLE 9

Ammonium glyphosate (32.0 g of an aqueous solution comprising 45.0% by weight of glyphosate acid equivalent and a molar ratio of ammonia to glyphosate of 1.9:1) was added to a water soluble polymer (2.0 g) in a 150 ml beaker and mixed using a mechanical stirrer, until the polymer dissolved/dispersed. To this solution/dispersion MORWET EFW (0.1 to 0.4 g, a wetter consisting of an alkyl naphthalene sulphonate from Witco) and ammonium sulphate (20.4 g, preground to a fine powder using a mortar and pestle and sieved using a 0.5 mm sieve) were added. The resultant dispersion was mixed thoroughly for approximately 5 minutes and the homogeneity of the slurry was observed. If 'salting out' had occurred, the slurry was discarded.

If a homogeneous slurry was obtained, the slurry was either cast using a "doctor blade" set at a blade height of 0.75 mm or poured and spread onto a polymer film (polythene) substrate. The wet tape was dried in an oven maintained at 95° C. until it was strippable from the substrate as a dry solid. The resultant solid contains approximately 41% glyphosate salt (37% glyphosate acid equivalent).

Flake thickness was measured using a micrometer screw gauge.

The dispersion time of the flakes was measured according to the procedure described in Example 1. A dispersion of the flakes in water was filtered through a 150 micron sieve (typical of a sieve used in connection with an agrochemical spray) and washed thoroughly in tap water (18° C.±2° C.). The surface of the sieve examined visually for residue.

Table 1 presents the results for the use of polymers according to the present invention whilst Table 2 presents comparative results when other polymers are used.

TABLE 1

| Polymer | Trade Name | Flake thickness (mm) | Dispersion Time (seconds) | Residue (150 micron sieve) |
|---|---|---|---|---|
| Copolymer of methyl vinyl ether/maleic anhydride with Average MW 216,000 | AGRIMER VEMA AN216 | 0.6–0.7 | 50 | No |
| Acid form of above with Average MW 240,000 | AGRIMER VEMA H240 | 2.5–4.0 | 45 | No |
| Acid form of above with Average MW 2,200,000 | AGRIMER VEMA H-2200 | 0.5 | 49 | No |
| Poly(acrylic acid-co-maleic acid) sodium salt | | 0.7–0.9 | 26 | No |
| Sulphonated polyvinyl alcohol, sodium salt | GOHSERAN L3266 | very soft | 48 | No |
| Sulphenated polystyrene, sodium salt | VERSA TL502 | 0.6–0.9 | 90 | No |
| Co-polymer of styrene/maleuc anhydride sulphonate, sodium salt | VERSA TL3 | 0.5–0.6 | 40 | No |
| Polyacrylic acid, sodium salt | | 0.5–0.7 | 26 | No |

TABLE 2

| Polymer | Trade Name | Flake thickness (mm) | Dispersion Time (seconds) | Residue (150 micron sieve) |
|---|---|---|---|---|
| Polyvinyl pyrrolidone | AGRIMER 30 | "Salted Out" | — | |
| Polyvinyl alcohol, 88% hydrolysed | | "Salted Out" | — | |
| Quaternized vinylpyrrolidone/dimethylaminoethyl methacrylate copolymer | AGRIMER DAQ-2000 | "Salted Out" | — | |
| Copolymer of vinylpyrrolidone/vinyl acetate | AGRIMER VA6 | "Salted Out" | — | |
| Hydroxyethyl cellulose | | 0.5 | 90 | Yes |
| Carboxymethyl cellulose | | 2.0–3.0 | 300 | Yes |
| Polyethylenimine | | 0.7–0.8 | 61 | Yes |
| Polyacrylamide | | brittle | 300+ | Yes |
| Carrageenan Type 2 | | 0.4 to 0.8 | 60 | Yes |
| Alginic acid, sodium salt | | 0.7 | 130 | Yes |
| Carbohydrate, Starch | PPE1259 | 0.6 | 120 | Yes |
| Xanthan gum | KELZAN S | 1.0–1.2 | 150 | Yes |

EXAMPLE 10

The procedure of Example 9 was repeated for AGRIMER VEMA AN216 with the exception that the amount of copolymer was increased from 2.0 g (5% w/w) to 8.0 g (20% w/w), and a corresponding decrease in ammonium sulphate content from 20.4 g to 14.4 g. Solid flakes of approximate thickness 0.7 mm, was obtained. The flakes dispersed readily in water (Temp: 21° C.; dispersion time: 25 seconds) leaving no residue.

EXAMPLE 11

Ammonium glyphosate (32.0 g of an aqueous solution comprising 45.0% by weight of glyphosate acid equivalent and a molar ratio of ammonia to glyphosate of 1.9:1) was added to AGRIMER VEMA AN-216 (2.0 g) in a 150 ml beaker and mixed using a mechanical stirrer, until the polymer dissolved/dispersed. To this solution/dispersion MORWET EFW (0.1 g, a wetter consisting of an alkyl naphthalene sulphonate from Witco) and Mergital LM17 (4.8 g) were added and mixed thoroughly using a mechanical stirrer. The filler (15.9 g) was added to the above dispersion and mixed for a further 5 minutes or until homogeneous.

The viscous film-forming medium was either cast using a "doctor blade" set at a blade height of 0.7 mm or poured and spread onto a polymer film (polythene) substrate. The wet tape was dried in an oven maintained at 95° C. until it was strippable from the substrate as a dry solid. The resultant solid contains approximately 41% glyphosate salt (37% glyphosate acid equivalent).

Flake thickness was measured using a micrometer screw gauge.

The dispersion time of the flakes was measured according to the procedure described in Example 1. A dispersion of the flakes in water was filtered through a 150 micron sieve and washed thoroughly in tap water (18° C.±2° C.) and the surface of the sieve examined visually for residue. The results are presented in Table 3.

TABLE 3

| Filler | Trade Name | Flake thickness (mm) | Dispersion Time (seconds) | Residue (150 micron sieve) |
|---|---|---|---|---|
| Ammonium sulphate | | 1.6–2.4 | 102 | No |
| Ammonium hydrogen phosphate | | 1.6–1.8 | 88 | No |
| Micro talc | | 0.5–0.8 | 72 | No |
| Attpulgite clay | ATTAGEL 50 | 0.3–0.4 | 70 | No |
| Microtalc : Ammonium sulphate (50 : 50) | | 0.6–0.7 | 40 | No |

EXAMPLE 12

Ammonium glyphosate (32.0 g of an aqueous solution comprising 45.0% by weight of glyphosate acid equivalent and a molar ratio of ammonia to glyphosate of 1.9:1) was added to AGRIMER VEMA AN-216 (2.0 g) in a 150 ml beaker and mixed using a mechanical stirrer, until the polymer dissolved/dispersed. To this solution/dispersion MORWET EFW (0.1 g) and adjuvant (4.8 g) were added and mixed thoroughly using a mechanical stirrer. Ammonium sulphate (15.9 g, preground to a fine powder using a mortar and pestle) was added to the above dispersion and mixed for a further 5 minutes or until homogeneous.

The viscous film-forming medium was either cast using a "doctor blade" set at a blade height of 0.75 mm or poured and spread onto a polymer film (polythene) substrate. The wet tape was dried in an oven maintained at 95° C. until it was strippable from the substrate as a dry solid. The resultant solid contains approximately 41% glyphosate salt (37% glyphosate acid equivalent).

Flake thickness was measured using a micrometer screw gauge.

The dispersion time of the flakes was measured according to the procedure described in Example 1. A dispersion of the flakes in water was filtered through a 150 micron sieve and washed thoroughly in tap water (18° C.±2° C.) and the surface of the sieve examined visually for residue.

TABLE 4

| Adjuvant | Trade Name | Flake thickness (mm) | Dispersion Time (seconds) | Residue (150 micron sieve) |
|---|---|---|---|---|
| $C_{10/14}$ alcohol ethoxylate with 17 moles EO | MERGITAL LM17 | 0.4–0.6 | 35 | No |
| Dimethylsiloxane glycol copolymer | SILWET co-polymer L7500 | 0.6–0.7 | 33 | No |
| Monobranched alcohol ethoxylate | ATLOX MBA 13/15 | 1.2–1.5 | 66 | No |
| Tallowamine ethoxylate with 15 moles EO | ETHOMEEN T25 | 0.6–0.7 | 91 | No |

EXAMPLE 13

The procedure of Example 12 was repeated for Mergital LM17 with the exception that the amount of adjuvant was increased from 4.8 g (12.4% w/w) to 20.0 g (51.7% w/w), and a corresponding decrease in ammonium sulphate content from 15.9 g to 0.7 g. Solid flakes of approximate thickness 0.31–0.5 mm, was obtained. The flakes dispersed readily in water (Temp: 19° C.; dispersion time: 80 seconds) leaving no residue.

EXAMPLE 14

AGRIMER VEMA AN-216 (40 g) was added to ammonium glyphosate (600 g of an aqueous solution containing 40% acid equivalent; ammonia:glyphosate acid=1.75:1.00), stirred using a mechanical stirrer and allowed to stand for approximately 20 minutes until the polymer had dissolved. To this solution, MERGITAL LM17 (80 g, $C_{10/14}$ alcohol ethoxylate with 17 moles EO, MERGITAL is a trademark of Henkel) and ammonium sulphate (280 g, pre-ground to a fine powder using a mortar and pestle) were added. The resultant dispersion was mixed thoroughly until a homogenous, viscous slurry was produced.

The viscous slurry was then diluted with water until the rheology of the slurry was suitable for processing in a spray drier. The slurry was spray-dried using disc atomisation in a Niro mobile minor. The inlet temperature was 160° C. and the outlet temperature was 60° C. A filamentous solid was obtained.

EXAMPLE 15

Diquat dibromide concentrate (26 g, 23.06% w/w diquat ions) was added to AGRIMER VEMA AN-216 (2 g) and mixed until all the polymer had dissolved. MORWET EFW (0.2 g) and talc (2 g) and magnesium sulphate monohydrate (2 g) were then added and mixed thoroughly until a homogenous slurry was produced.

The resultant slurry was then poured into a petri dish and placed in an oven maintained at a 50° C. A dry, water dispersible solid comprising approximately 34.5% diquat ions (64.4% diquat salt) was obtained.

What is claimed is:

1. A process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer which is a partially or fully charged homopolymer or a partially charged block copolymer or a homopolymer or block copolymer capable of ring-opening to form a partially charged homopolymer or block copolymer and (b) a water soluble material which is non film-forming and thereafter (ii) drying the film-forming aqueous medium to form the solid composition, wherein the film-forming aqueous medium is prepared using water as the sole medium for both the film-forming polymer (a) and the water-soluble material (b) and wherein the film-forming polymer is selected from the group consisting of an alkyl vinylether maleic anhydride block co-polymer, a hydrolysed alkyl vinylether maleic anhydride block co-polymer, a salt of poly (acrylic acid/maleic acid) copolymer, a salt of sulphonated poly (styrene/maleic anhydride) copolymer, a salt of sulphonated polystyrene and a salt of sulphonated polyvinyl alcohol.

2. A process according to claim 1 wherein the water soluble material which is non film-forming is a salt of glyphosate, a bipyridylium salt, glufosinate, fomesafen or ammonium sulphate.

3. A process according to claim 1 wherein the film-forming polymer is an alkyl vinylether maleic anhydride block co-polymer having a number average molecular weight of from 20,000 to 990,000 or is a hydrolysed alkyl vinylether maleic anhydride block co-polymer having a molecular weight from 20,000 to 3,000,000.

4. A process according to claim 1 wherein the water-soluble material is a salt of glyphosate, the film-forming medium is an alkyl vinylether maleic anhydride co-polymer and there is incorporated in the film-forming medium an ammonium salt in the substantial absence of an inert filler.

5. A process according to claim 1 wherein there is included an inert inorganic filler.

6. A process according to claim 1 wherein the concentration of the film-forming polymer in the film-forming aqueous medium is from 0.5 to 96% by weight.

7. A process according to claim 1 wherein the content of the water soluble supported material in the solid composition of the invention is greater than 40% by weight.

8. A solid, water-soluble or water-dispersible composition comprising a glyphosate salt, an alkyl vinylether maleic anhydride block co-polymer or a hydrolysed derivative thereof and ammonium sulphate.

* * * * *